United States Patent
Wang et al.

(10) Patent No.: US 6,850,846 B2
(45) Date of Patent: Feb. 1, 2005

(54) COMPUTER SOFTWARE FOR GENOTYPING ANALYSIS USING PATTERN RECOGNITION

(75) Inventors: Eugene Wang, Milpitas, CA (US); Teresa Webster, Loma Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 99 days.

(21) Appl. No.: 09/758,872

(22) Filed: Jan. 11, 2001

(65) Prior Publication Data

US 2002/0016680 A1 Feb. 7, 2002

Related U.S. Application Data

(60) Provisional application No. 60/175,567, filed on Jan. 11, 2000.

(51) Int. Cl.[7] .............................................. G01N 33/48
(52) U.S. Cl. ................ 702/19; 702/20; 435/6
(58) Field of Search ......................... 702/19, 20; 435/6

(56) References Cited

U.S. PATENT DOCUMENTS 5,858,659 A * 1/1999 Sapolsky et al. ............... 435/6

OTHER PUBLICATIONS

Wang et al, Science 280: 1077 (1998).*
Lockhart et al, Nature Biotechnology 14: 1675 (1996).*

* cited by examiner

*Primary Examiner*—James Martinell
(74) *Attorney, Agent, or Firm*—Wei Zhou; Philip L. McGarrigle; Priyadarshini Rath

(57) ABSTRACT

Methods, systems and computer software products are provided for determining genotype of a sample using a plurality of probes. In one preferred embodiment, a tentative genotype call is made based upon the relative allele signals. Pattern recognition is then used to validate the tentative call.

45 Claims, 5 Drawing Sheets

COMPUTER SOFTWARE FOR GENOTYPING ANALYSIS USING PATTERN RECOGNITION

RELATED APPLICATIONS

This application claims the priority of U.S. Provisional Application No. 60/175,567, filed on Jan. 11, 2000. The '567 application is incorporated herein by reference for all purposes.

FIELD OF INVENTION

This invention is related to bioinformatics and biological data analysis. Specifically, this invention provides methods, computer software products and systems for analyzing genotyping data.

BACKGROUND OF THE INVENTION

Single nucleotide polymorphism (SNP) has been used extensively for genetic analysis. Fast and reliable hybridization-based SNP assays have been developed. (See Wang et al., Large-Scale Identification, Mapping, and Genotyping of Single-Nucleotide Polymorphism's in the Human Genome, Science 280:1077–1082, 1998; Gingeras, et al., Simultaneous Genotyping and Species Identification Using Hybridization Pattern Recognition Analysis of Generic Mycobacterium DNA Arrays, Genome Research 8:435–448, 1998; Halushka, et al., Patterns of Single-Nucleotide Polymorphisms in Candidate Genes for Blood-Pressure Homeostasis, Nature Genetics 22:239–247, 1999; all incorporated herein by reference in their entireties. Computer-implemented methods for discovering polymorphism and determining genotypes are disclosed in, e.g., U.S. Pat. No. 5,858,659, incorporated herein by reference in its entirety for all purposes. However, there is still need for additional methods for determining genotypes.

SUMMARY OF THE INVENTION

In one aspect of the invention, methods, preferably computer implemented, are provided to determine the genotypes of a nucleic acid sample. In preferred embodiments, the methods include obtaining a plurality of sample probe intensities reflecting the hybridization between the sample and a plurality of probes; determining a tentative genotype based upon the sample probe intensities; and accepting the tentative genotype as the genotype of the sample if the pattern of the sample probe intensities is similar to that of reference probe intensities for the tentative genotype. Preferred methods for determining the similarity of probe intensity patterns include evaluating the linear correlation coefficient between probe intensities. In preferred embodiments, the accepting step includes calculating linear correlation coefficient between the sample probe intensities and reference probe intensities; and accepting the tentative genotype as the genotype of the sample if the linear correlation coefficient is greater than a threshold value. The threshold value may be at least 0.8, 0.9, or 0.95. In one particularly preferred embodiment, the tentative genotype is determined based upon a relative allele signal calculated using the sample probe intensities.

The probes are preferably immobilized on a substrate at a density of at least 400 probes per $cm^2$, more preferably at a density of at least 1000 probes per $cm^2$. The reference genotype can be either a homozygous genotype or a heterozygous genotype. In preferred embodiments, the probes contain perfect match probes that are designed to be perfect match for a first genotype (A) and a second genotype (B). In addition, the probes contain mismatch probes that are designed to be mismatch for a first genotype and a second genotype.

In another aspect of the invention, methods are provided to determine the genotype of a sample using pattern recognition directly, without first determining a tentative genotype. The methods include obtaining a plurality of sample probe intensities reflecting the hybridization between the sample and a plurality of probes; and determining whether the pattern of the sample probe intensities is similar to that of reference probe intensities, wherein the reference probe intensities reflect the hybridization between the plurality of probes and a reference sample having a reference genotype. In preferred embodiments, the determining step includes calculating a linear correlation coefficient between the sample probe intensities and reference probe intensities; and indicating that the genotype of the sample is the same as the reference genotype, if the correlation coefficient is greater than a threshold value, which is at least 0.8, 0.9 or 0.95.

In yet another aspect of the invention, system and computer software for determining genotypes are provided. The systems include a processor; and a memory coupled with the processor, the memory storing a plurality of machine instructions that cause the processor to perform logical steps of the methods of the invention. The computer software products of the invention include a computer readable medium having computer-executable instructions for performing the methods of the invention.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Figure 1:
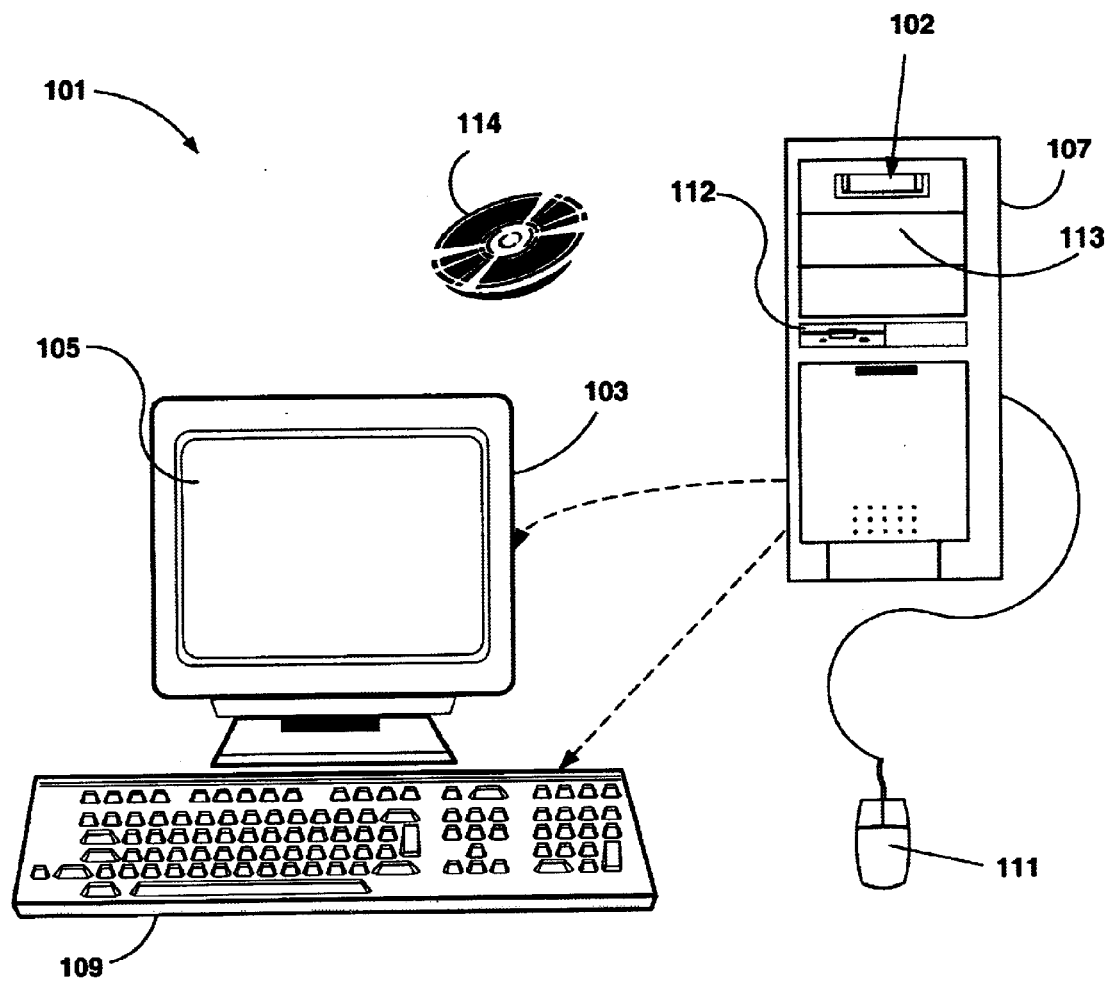
FIG. 1 illustrates an example of a computer system that may be utilized to execute the software of an embodiment of the invention.

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention. All cited references, including patent and non-patent literature, are incorporated herein by reference in their entireties for all purposes.

I. High Density Probe Arrays

The methods, computer software and systems of the invention are particularly useful for analyzing genotyping data generated using high density probe arrays, such as high density nucleic acid probe arrays.

High density nucleic acid probe arrays, also referred to as "DNA Microarrays," have become a method of choice for monitoring the expression of a large number of genes and for detecting sequence variations, mutations and polymorphism. As used herein, "nucleic acids" may include any polymer or oligomer of nucleosides or nucleotides (polynucleotides or oligonucleotidies), which include pyriridine and purine bases, preferably cytosine, thyrine, and uracil, and adenine and guanine, respectively. (See Albert L. Lehninger, PRINCIPLES OF BIOCHEMISTRY, at 793–800 (Worth Pub. 1982) and L. Stryer, BIOCHEMISTRY, 4$^{th}$ Ed (March 1995), both incorporated by reference.) "Nucleic acids" may include any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

"A target molecule" refers to a biological molecule of interest. The biological molecule of interest can be a ligand, receptor, peptide, nucleic acid (oligonucleotide or polynucleotide of RNA or DNA), or any other of the biological molecules listed in U.S. Pat. No. 5,445,934 at col. 5, line 66 to col. 7, line 51, which is incorporated herein by reference for all purposes. For example, if transcripts of genes are the interest of an experiment, the target molecules would be the transcripts. Other examples include protein fragments, small molecules, etc. "Target nucleic acid" refers to a nucleic acid (often derived from a biological sample) of interest. Frequently, a target molecule is detected using one or more probes. As used herein, a "probe" is a molecule for detecting a target molecule. It can be any of the molecules in the same classes as the target referred to above. A probe may refer to a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e., A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

In preferred embodiments, probes may be immobilized on substrates to create an array. An "array" may comprise a solid support with peptide or nucleic acid or other molecular probes attached to the support. Arrays typically comprise a plurality of different nucleic acids or peptide probes that are coupled to a surface of a substrate in different, known locations. These arrays, also described as "microarrays" or colloquially "chips" have been generally described in the art, for example, in Fodor et al., Science, 251:767–777 (1991), which is incorporated by reference for all purposes. Methods of forming high density arrays of oligonucleotides, peptides and other polymer sequences with a minimal number of synthetic steps are disclosed in, for example, U.S. Pat. Nos. 5,143,854, 5,252,743, 5,384,261, 5,405,783, 5,424,186, 5,429,807, 5,445,943, 5,510,270, 5,677,195, 5,571,639, 6,040,138, all incorporated herein by reference for all purposes. The oligonucleotide analogue array can be synthesized on a solid substrate by a variety of methods, including, but not limited to, light-directed chemical coupling, and mechanically directed coupling. (See Pirrung et al., U.S. Pat. No. 5,143,854, PCT Application No. WO 90/15070) and Fodor et al., PCT Publication Nos. WO 92/10092 and WO 93/09668, U.S. Pat. Nos. 5,677,195, 5,800,992 and 6,156, 501, which disclose methods of forming vast arrays of peptides, oligonucleotides and other molecules using, for example, light-directed synthesis techniques.) (See also Fodor, et al., Science, 251, 767–77 (1991)). These procedures for synthesis of polymer arrays are now referred to as VLSIPS™ procedures.

Methods for making and using molecular probe arrays, particularly nucleic acid probe arrays are also disclosed in, for example, U.S. Pat. Nos. 5,143,854, 5,242,974, 5,252, 743, 5,324,633, 5,384,261, 5,405,783, 5,409,810, 5,412,087, 5,424,186, 5,429,807, 5,445,934, 5,451,683, 5,482,867, 5,489,678, 5,491,074, 5,510,270, 5,527,681, 5,527,681, 5,541,061, 5,550,215, 5,554,501, 5,556,752, 5,556,961, 5,571,639, 5,583,211, 5,593,839, 5,599,695, 5,607,832, 5,624,711, 5,677,195, 5,744,101, 5,744,305, 5,753,788, 5,770,456, 5,770,722, 5,831,070, 5,856,101, 5,885,837, 5,889,165, 5,919,523, 5,922,591, 5,925,517, 5,658,734, 6,022,963, 6,150,147, 6,147,205, 6,153,743 and 6,140,044, all of which are incorporated by reference in their entireties for all purposes.

Microarrays can be used in a variety of ways. A preferred microarray contains nucleic acids and is used to analyze nucleic acid samples. Typically, a nucleic acid sample is prepared from appropriate source and labeled with a signal moiety, such as a fluorescent label. The sample is hybridized with the array under appropriate conditions. The arrays are washed or otherwise processed to remove non-hybridized sample nucleic acids. The hybridization is then evaluated by detecting the distribution of the label on the chip. The distribution of label may be detected by scanning the arrays to determine fluorescence intensity distribution. Typically, the hybridization of each probe is reflected by several pixel intensities. The raw intensity data may be stored in a gray scale pixel intensity file. The GATC™ Consortium has specified several file formats for storing array intensity data. The final software specification is available at the Consortium's website and is incorporated herein by reference in its entirety. The pixel intensity files are usually large. For example, a GATC™ compatible image file may be approximately 50 Mb if there are about 5000 pixels on each of the horizontal and vertical axes and if a two byte integer is used for every pixel intensity. The pixels may be grouped into cells. (See GATC™ software specification). The probes in a cell are designed to have the same sequence; i.e., each cell is a probe area A CEL file contains the statistics of a cell, e.g., the 75th percentile and standard deviation of intensities of pixels in a cell. The 50, 60, 70, 75 or 80th percentile of pixel intensity of a cell is often used as the intensity of the cell.

Methods for signal detection and processing of intensity data are additionally disclosed in, for example, U.S. Pat. Nos. 5,445,934, 547,839, 5,578,832, 5,631,734, 5,800,992, 5,856,092, 5,936,324, 5,981,956, 6,025,601, 6,090,555, 6,141,096, 6,141,096, and 5,902,723. Methods for array based assays, computer software for data analysis and applications are additionally disclosed in, e.g., U.S. Pat. Nos. 5,527,670, 5,527,676, 5,545,531, 5,622,829, 5,631,128, 5,639,423, 5,646,039, 5,650,268, 5,654,155, 5,674,742, 5,710,000, 5,733,729, 5,795,716, 5,814,450, 5,821,328, 5,824,477, 5,834,252, 5,834,758, 5,837,832, 5,843,655, 5,856,086, 5,856,104, 5,856,174, 5,858,659, 5,861,242, 5,869,244, 5,871,928, 5,874,219, 5,902,723, 5,925,525, 5,928,905, 5,935,793, 5,945,334, 5,959,098, 5,968,730, 5,968,740, 5,974,164, 5,981,174, 5,981,185, 5,985,651, 6,013,440, 6,013,449, 6,020,135, 6,027,880, 6,027,894, 6,033,850, 6,033,860, 6,037,124, 6,040,138, 6,040,193, 6,043,080, 6,045,996, 6,050,719, 6,066,454, 6,083,697, 6,114,116, 6,114,122, 6,121,048, 6,124,102, 6,130,046, 6,132,580, 6,132,996 and 6,136,269, all of which are incorporated by reference in their entireties for all purposes.

Nucleic acid probe array technology, use of such arrays, analysis array based experiments, associated computer software, composition for making the array and practical applications of the nucleic acid arrays are also disclosed, for example, in the following U.S. patent applications: Ser. Nos. 07/838,607, 07/883,327, 07/978,940, 08/030,138, 08/082,937, 08/143,312, 08/327,522, 08/376,963, 08/440,742, 08/533,582, 08/643,822, 08/772,376, 09/013,596, 09/016,564, 09/019,882, 091020,743, 09/030,028, 09/045,547, 09/060,922, 09/063,311, 09/076,575, 09/079,324, 09/086,285, 09/093,947, 09/097,675, 09/102,167, 09/102,986, 09/122,167, 09/122,169, 09/122,216, 09/122,304, 09/122,434, 09/126,645, 09/127,115, 09/132,368, 09/134,758, 09/138,958, 09/146,969, 09/148,210, 09/148,813, 09/170,847, 09/172,190, 09/174,364, 09/199,655, 09/203,677, 09/256,301, 09/285,658, 09/294,293, 09/318,775, 09/326,137, 09/326,374, 09/341,302, 09/354,935, 09/358,664, 09/373,984, 09/377,907, 09/383,986, 09/394,230, 09/396,196, 09/418,044, 09/418,946, 09/420,805, 09/428,350, 09/431,964, 09/445,734, 09/464,350, 09/475,209, 09/502,048, 09/510,643, 09/513,300, 09/516,388, 09/528,414, 09/535,142, 09/544,627, 09/620,780, 09/640,962, 09/641,081, 09/670,510, 09/685,011, and 09/693,204 and in the following Patent Cooperative Treaty (PCT) applications/publications: PCT/NL90/00081 PCT/GB91/00066, PCT/US91/08693, PCT/US91/09226, PCT/US91/09217, WO/93/10161, PCT/US92/10183, PCT/GB93/00147, PCT/US93/01152, WO/93/22680, PCT/US93/04145, PCT/US93/08015, PCT/US94/07106, PCT/US94/12305, PCT/GB95/00542, PCT/US95/07377, PCT/US95/02024, PCT/US96/05480, PCT/US96/11147, PCT/US96/14839, PCT/US96/15606, PCT/US97/01603, PCT/US97/02102, PCT/GB97/005566, PCT/US97/06535, PCT/GB97/01148, PCT/GB97/01258, PCT/US97/08319, PCT/US97/08446, PCT/US97/10365, PCT/US97/17002, PCT/US97/16738, PCT/US97/19665, PCT/US97/20313, PCT/US97/21209, PCT/US97/21782, PCT/US97/23360, PCT/US98/06414, PCT/US98/01206, PCT/GB98/00975, PCT/US98/04280, PCT/US98/04571, PCT/US98/05438, PCT/US98/05451, PCT/US98/12442, PCT/US98/12779, PCT/US98/12930, PCT/US98/13949, PCT/US98/15151, PCT/US98/15469, PCT/US98/15458, PCT/US98/15456, PCT/US98/16971, PCT/US98/16686, PCT/US99/19069, PCT/US98/18873, PCT/US98/18541, PCT/US98/19325, PCT/US98/22966, PCT/US98/26925, PCT/US98/27405 and PCT/IB99/00048, all the above cited patent applications and other references cited throughout this specification are incorporated herein by reference in their entireties for all purposes.

II. Genotyping and Polymorphism Detection Using High Density Probe Arrays

Genotyping involves determining the identity of alleles for a gene or polymorphic marker possessed by an individual. Genotyping of individuals and populations has many uses. Genetic information about an individual can be used for diagnosing the existence or predisposition to conditions to which genetic factors contribute. Many conditions result not from the influence of a single allele, but involve the contributions of many genes. Therefore, determining the genotype for several genes can be useful for diagnosing complex genetic conditions.

Genotyping of many loci from a single individual also can be used in forensic applications, for example, to identify an individual based on biological samples from the individual. Genotyping of populations is useful in population genetics. For example, the tracking of frequencies of various alleles in a population can provide important information about the history of a population or its genetic transformation over time. For a general review of genotyping and its use. (See Diagnostic Molecular Pathology: A Practical Approach: Cell and Tissue Genotyping (Practical Approach Series) by James O'Donnell McGee (Editor), C. S. Herrington (Editor), ISBN: 0199632383 and SNP and Microsatellite Genotyping: Markers for Genetic Analysis (Biotechniques Molecular Laboratory Methods Series.) by Ali Hajeer (Editor), Jane Worthington (Editor), Sally John (Editor), ISBN 1881299384, both are incorporated herein by reference in their entireties.)

Determining the genotype of a sample of genomic material according to the methods of the present invention, is generally carried out using arrays of oligonucleotide probes. These arrays may generally be "tiled" for a large number of specific polymorphisms. "Tiling," as used herein, refers to the synthesis of a defined set of oligonucleotide probes which is made up of a sequence complementary to the target sequence of interest, as well as preselected variations of that sequence, e.g., substitution of one or more given positions with one or more members of the basis set of monomers, i.e., nucleotides. Tiling strategies are discussed in detail in, for example, Published PCT Application No. WO 95/11995, incorporated herein by reference in its entirety for all purposes. "Target sequence," as used herein, refers to a sequence which has been identified as containing a polymorphism, and more preferably, a single-base polymorphism, also referred to as a "biallelic base." It will be understood that the term "target sequence" is intended to encompass the various forms present in a particular sample of genomic material, i.e., both alleles in a diploid genome.

One of skill in the art would appreciate that the methods, software and systems of the invention are not limited to any particular tiling format. In exemplary embodiments, arrays are tiled for a number of specific, identified polymorphic marker sequences. In particular, the array is tiled to include a number of detection blocks, each detection block being specific for a specific polymorphic marker or set of polymorphic markers. For example, a detection block may be tiled to include a number of probes which span the sequence segment that includes a specific polymorphism. To ensure probes that are complementary to each variant, the probes are synthesized in pairs differing at the biallelic base.

In addition to the probes differing at the biallelic bases, monosubstituted probes are also generally tiled within the detection block. These monosubstituted probes have bases at and up to a certain number of bases in either direction from the polymorphism, substituted with the remaining nucleotides (selected from A, T, G, C or U). Typically, the probes in a tiled detection block will include substitutions of the sequence positions up to and including those that are 3, 4, 5, 6, 7, 8 or 9 bases away from the base that corresponds to the polymorphism. Preferably, bases up to and including those in positions 2, 3, 4, 5, 6, 7, 8 or 9 bases from the polymorphism will be substituted. The monosubstituted probes provide internal controls for the tiled array, to distinguish actual hybridization from artifactual cross-hybridization. A variety of tiling configurations may also be employed to ensure optimal discrimination of perfectly hybridizing probes. For example, a detection block may be tiled to provide probes having optimal hybridization intensities with minimal cross-hybridization. For example, where a sequence downstream from a polymorphic base is G-C rich, it could potentially give rise to a higher level of cross-hybridization or "noise," when analyzed. Accordingly, one can tile the detection block to take advantage of more of the upstream sequence.

Optimal tiling configurations may be determined for any particular polymorphism by comparative analysis. Additionally, arrays will generally be tiled to provide for ease of reading and analysis. For example, the probes tiled within a detection block will generally be arranged so that reading across a detection block the probes are tiled in succession, i.e., progressing along the target sequence one or more base at a time.

Once an array is appropriately tiled for a given polymorphism or set of polymorphisms, the target nucleic acid is hybridized with the array and scanned. Hybridization and scanning are generally carried out by methods described in, e.g., Published PCT Application Nos. WO 92/10092 and WO 95/11995, and U.S. Pat. Nos. 5,445,934 and 5,424,186, incorporated herein by reference in their entirety for all purposes. In brief, a target nucleic acid sequence which includes one or more previously identified polymorphic markers is amplified by well known amplification techniques, e.g., polymerase chain reaction (PCR), ligation chain reaction (LCR), and Rolling Circle Amplification. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hyridization data obtained from the scan is typically in the form of fluorescence intensities as a function of location on the array.

Although primarily described in terms of a single detection block, e.g., for detection of a single polymorphism, in preferred aspects, the arrays of the invention will include multiple detection blocks, and thus be capable of analyzing multiple, specific polymorphisms. For example, preferred arrays will generally include from about 50, 100, 500, 1000, 2000, 3000 to about 4000 or more different detection blocks with particularly preferred arrays including from 100 to 3000 different detection blocks. In addition, for each marker, there may be two detection blocks, one for the sense and another for the antisense strand of the allele.

In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

III. Systems for Genotyping Calls

Methods, computer software and systems for making genotyping calls using probe intensities are provided. One of skill in the art would appreciate that many computer systems are suitable for carrying out the genotyping methods of the invention. Computer software according to the embodiments of the invention can be executed in a wide variety of computer systems.

For a description of basic computer systems and computer networks. (See Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337, both are incorporated herein by reference in their entireties for all purposes.

FIG. 1 illustrates an example of a computer system that may be used to execute the software of an embodiment of the invention. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a floppy drive 112, CD-ROM or DVD-ROM drive 102, system memory and a hard drive (113) (see also FIG. 2) which may be utilized to store and retrieve software programs incorporating computer code that implements the invention, data for use with the invention and the like Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
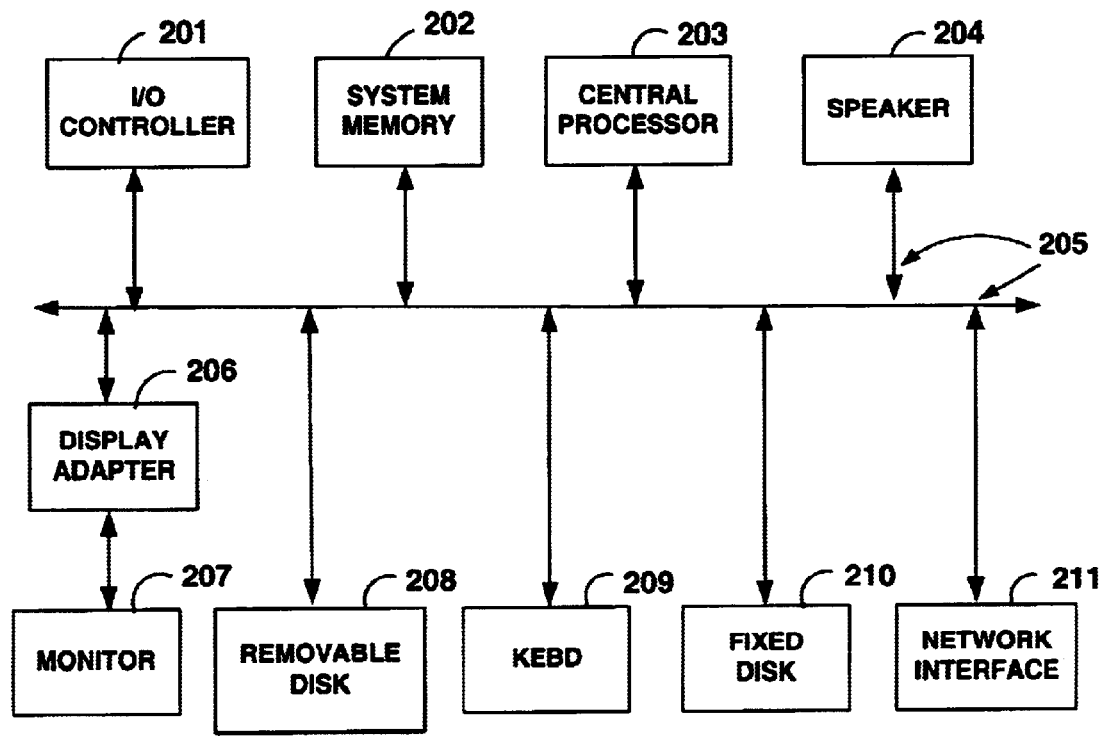
FIG. 2 illustrates a system block diagram of the computer system of FIG. 1.

FIG. 2 shows a system block diagram of computer system 101 used to execute the software of an embodiment of the invention. As in FIG. 1, computer system 101 includes monitor 201, and keyboard 209. Computer system 101 further includes subsystems such as a central processor 203 (such as a Pentium™ III processor from Intel), system memory 202, fixed storage 210 (e.g., hard drive), removable storage 208 (e.g., floppy or CD-ROM), display adapter 206, speakers 204, and network interface 211. Other computer systems suitable for use with the invention may include additional or fewer subsystems. For example, another computer system may include more than one processor 203 or a cache memory. Computer systems suitable for use with the invention may also be embedded in a measurement instrument.

Figure 3:
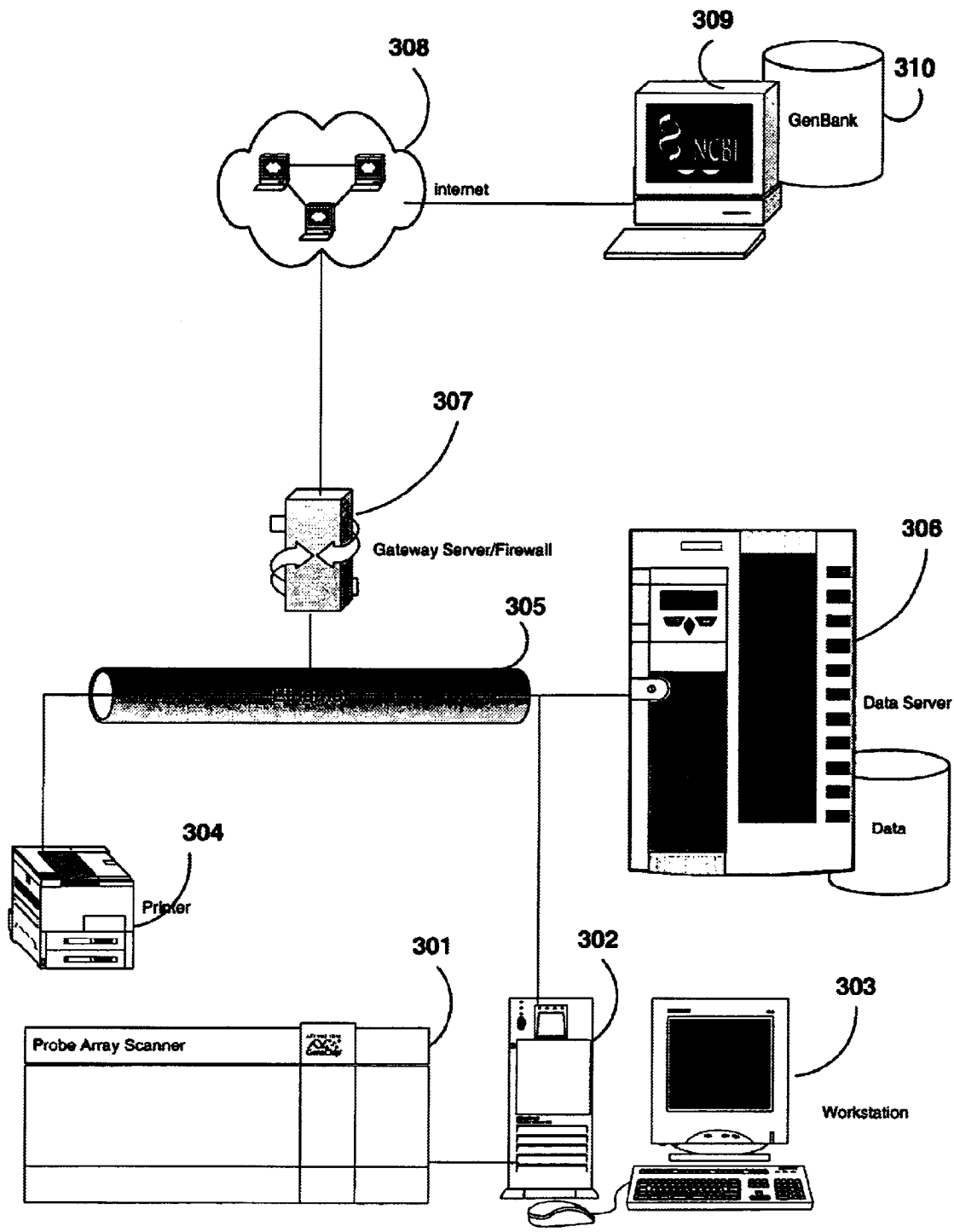
FIG. 3 illustrates a computer network suitable for executing the software of an embodiment of the invention.

FIG. 3 shows an exemplary computer network that is suitable for executing the computer software of the invention. A computer workstation 302 is connected with and controls a probe array scanner 301. Probe intensities are acquired from the scanner and may be displayed in a monitor 303. The intensities may be processed to make genotype calls (i.e., determining the genotype based upon probe intensities) on the workstation 302. The intensities may be processed and stored in the workstation or in a data server 306. The workstation may be connected with the data server through a local area network (LAN), such as an Ethernet 305. A printer 304 may be connected directly to the workstation or to the Ethernet 305. The LAN may be connected to a wide area network (WAN), such as the Internet 308, via a gateway server 307 which may also serve as a firewall between the WAN 308 and the LAN 305. In preferred embodiments, the workstation may communicate with outside data sources, such as the National Biotechnology Information Center, through the Internet. Various protocols, such as FTP and HTTP, may be used for data communication between the workstation and the outside data sources. Outside genetic data sources, such as the GenBank 310, are well known to those skilled in the art. An overview of GenBank and the National Center for Biotechnology Information (MCBI) can be found on the web site of NCBI.

IV. Genotyping Call Methods and Software

The methods of the invention are generally described in the context of determining genotype for a marker. However, the preferred embodiments may involve the determination of multiple markers, preferably at least 10 markers, more preferably at least 100 markers, most preferably, at least 500, 1000, 2000, 3000, 4000 or more markers. The process for determining genotypes for multiple markers may involve repeating the method steps for determining genotype for a single marker for all the markers. The process may involve sequentially determining genotypes for each marker. Alternatively, the genotype of multiple markers may be determined in parallel.

Figure 4:
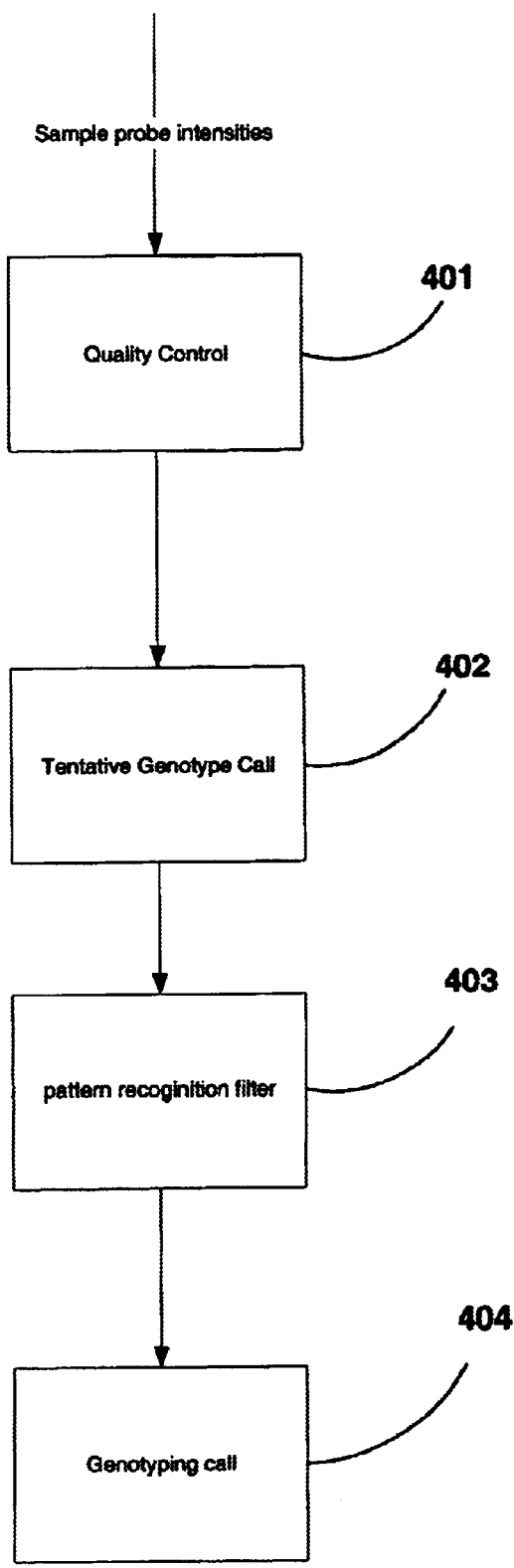
FIG. 4 illustrates a process for calling genotypes.

FIG. 4 shows a process for determining genotypes. The exemplary methods use probe intensities for determining genotypes (making a genotyping call or a genotype call). The probes are preferably oligonucleotide probes immobilized on a substrate in high density format ie., at least 400 probes/cm$^2$ or at least 1000 probes/cm$^2$. However, the methods, system and software of the invention are not limited to the format of probes. For example, the methods are useful for genotyping calls using probes immobilized on optical fibers or beads or other substrates shown in U. S. Pat. No. 5,445,934, which is incorporated herein by reference in its entirety. The methods are also useful for analyzing genotyping hybridization assays using immobilized sample and solution phase probes.

Probe intensities are inputted and examined by a quality control process 401. The quality control process is optional and generally, it enhances the accuracy of genotyping calls. U.S. Pat. No. 5,858,659 and U.S. patent application Ser. No. 08/853,370, filed on May 8, 1997, disclose some embodiments of the quality control processes. Both the '659 patent and the '370 application are incorporated herein in their entireties by reference for all purposes.

In some embodiments, where the arrays are designed with both prefect match and mismatch probes, the quality control process may involve evaluating whether the probe sets detect genuine signal. In preferred embodiments, a ratio of perfect match intensity over mismatch intensity is evaluated and if the ratio is above a threshold or cutoff value, the probe set is determined to have passed the quality control process. In general, the ratio should beat least 1.0, preferably, at least 1.1, 1.2, 1.3, 1.4, 1.5, 1.6, 1.7, 1.8, 1.9, more preferably, at least 2.0. As described above, there are generally at least two probe sets for determining an allele, i.e., PMa/MMa (for allele A) and PMb/MMb (for allele B). There could be multiple PMa/MMa or PMb/MMb probe pairs for a single allele. Probes may be organized as blocks (each block may contain sense or antisense probes) and miniblocks (each miniblock may contain a PMa/MMa probe pair and a PMb/MMb probe pair).

In an exemplary quality control process, if either the PMa/MMa or PMb/MMb probe pair in a miniblock has a ratio above the threshold value, the miniblock passes the quality control.

In some particularly preferred embodiments, probe intensities are evaluated according to: (PMa+PMb−mean)/Std>StdDevCut, where:

$$mean = \left(\sum_{i=1}^{Nmm} MMi\right) / Nmm;$$

Nmm=number of MM probes (both for allele A and B) for the block; MMi=the intensity of MM probe i; and $$Std = \sqrt{\left(\sum_{i=1}^{Nmm} (MMi - mean)^2\right) / (Nmm - 1)}.$$

The StdDevCut may be generally above 1.0, preferably at least 1.1, 1.2, 1.3, 1.4, 1.5, 1.6, 1.7, 1.8, 1.9, more preferably at least 2.0.

In addition to the quality control process, the intensity values may be processed to account for scanning at different wavelength to increase the dynamic range of the scanner. For example, some fluorescence intensity values may be obtained by scanning at 530 nm and 570 nm. The 530 nm data may be extrapolated to intensities at 570 nm. Methods for increasing dynamic range by scanning at different wavelengths are disclosed in, e.g., U.S. Pat. No. 6,171,793, which is incorporated herein in its entirety by reference for all purposes.

Continuing on FIG. 4, after intensity values are optionally evaluated for quality control purpose, the intensity values are used to calculate a relative allele signal to determine a tentative genotype call 402. The relative allele signal reflects the hybridization of sample nucleic acid and the allele specific probe(s). For example, in some embodiments, the relative allele signal increases when hybridization with the A allele specific probe increases, i.e., a high value indicates an AA genotype; a medium value indicates an AB genotype; and a low value indicates a BB genotype. One of skill in the art would appreciate that the designation of Allele A versus B may be arbitrary. In general, the relative allele signal is a function of the probe intensities and the value of the relative allele signal tends to shift toward one end when the sample has a homozygous genotype (AA or BB).

In a particularly preferred embodiments, the indicator, $\hat{P}$, is calculated as follows for a block:

$$\hat{P} = \frac{AveDa}{AveDa + AveDb}$$

where:

$$AveDa = \frac{\sum_{i=1}^{m} \max(0, Da)}{m} \text{ and } AveDb = \frac{\sum_{i=1}^{m} \max(0, Db)}{m};$$

and

Da=PMa−max(MMa, MMb) and Db=PMb−max(MMa, MMb); This and m=number of miniblocks.

The value of $\hat{p}$ should be between 0.0 and 1.0. A large $\hat{p}$ value would result if the sample hybridizes strongly with allele A (arbitrary designated) specific probes only. Similarly, a small $\hat{p}$ value would result if the sample hybridizes strongly with allele B only. A medium $\hat{p}$ value would result if the sample hybridizes strongly with both alleles.

One of skill in the art would appreciate that the methods of the invention are not limited to any particular formulation for indicator calculation. Rather, a whole range of possible indicator formulations are suitable for the methods of the invention.

In one aspect of the invention, methods are provided to make genotyping calls using the indicator. In some embodiments, the calls are made by comparing the relative allele signal with reference zones for genotypes AA, AB and BB.

There are typically three reference zones, AA, AB and BB. Between the zones, there are "no call" gaps. If the relative allele signal falls into one of the zones, a genotyping call is made according to which zone the relative allele signal falls. If the relative allele signal falls into the no call gaps, a genotype call is not made. In the software products of the invention, the reference zones may be user adjustable, e.g., inputted from files. One of skill in the art would appreciate that the zone settings affect the accuracy of calls. Generally, more stringent zone settings, i.e., smaller zones with bigger "no call" gaps, would result in higher accuracy, but also higher number of no calls. In one particularly preferred embodiment, the no call gap is about 0.01, 0.02, 0.03, 0.04, 0.05, 0.06, 0.07, 0.08, 0.09 or 0.10.

The following pseudo code illustrates a computerized process for genotype lookup for a single marker. The process may be repeated for multiple markers.

IF no block passes the QC
THEN genotype="NoSignal"
DONE
ELSE
Let the following values be imported:
Sa=Mid point of Sense Block M $\hat{P}$ Cluster
Sab=Mid point of Sense Block AB $\hat{P}$ Cluster
Sb=Mid point Sense Block BB $\hat{P}$ Cluster
Aa=Mid point of AntiSense Block AA $\hat{P}$ Cluster
Aab=Mid point of Antisense Block AB $\hat{P}$ Cluster
Ab=Mid point of Antisense Block BB $\hat{P}$ Cluster Let
S=$\hat{P}$ value of a sense block of a sample
A=$\hat{P}$ value of an anti-sense block of a sample
IF there is only one block for the marker or IF only one block passes the QC test THEN
   Dist-A=abs(S-Sa) OR abs(A-Aa)
   Dist__AB=abs(S-Sab) OR abs(A-Aab)
   Dist__BB=abs(S-Sb) OR abs(A-Ab)

| | |
|---|---|
| ELSE IF there are both sense and antisense block | |
| | Dis__A=sqrt((S-Sa)$^2$+(A-Aa)$^2$) |
| | Dist__AB=sqrt((S-Sab)$^2$+(A-Aab)$^2$) |
| | Dist__B=sqrt((S-Sb)$^2$+(A-Ab)$^2$) |
| LOOKUP | MinDist=min(Dist__A, Dist__AB, Dist__B) |
| | SecondDist=second(Dist__A, Dist__AB, Dist__B) |
| | MaxDist=max(Dist__A, Dist__AB, Dist__B) |

IF $\hat{P}$ is not in the no call gaps

| | |
|---|---|
| THEN ASSIGN genotype, | |
| Where | |
| | MinDist=Dist__A, THEN genotype="AA" |
| | MinDist=Dist__AB, THEN genotype="AB" |
| | MinDist=Dist__B, THEN genotype="BB" |
| ELSE IF | ($\hat{P}$ is in No Call GAP) and ((MinDist=Dist__AB AND SecondDist=Dist__A) OR(MinDist=Dist__A AND SecondDist=Dist__AB)) genotype="AB_A" |
| ELSE IF | ($\hat{P}$ is in No Call GAP) and ((MinDist=Dist__AB AND SecondDist=Dist__B) OR (MinDist=Dist__B AND SecondDist=Dist__AB)) genotype="AB_B" |

In some instances, genotyping calls based upon relative allele signals are subject to experimental noises so that incorrect genotyping calls may be made. In one aspect of the invention, methods, system and computer software products are provided to filter out genotyping calls that are likely the result of experimental noises 403. In preferred embodiments, genotyping calls based upon relative allele signals are invalidated (or filtered out) if the sample probe intensity patterns are significantly different from the reference probe intensity patterns for the genotype. For example, if a BB genotype is called using relative allele signal. The reference probe intensities for the BB genotype are inputted. The pattern of the reference probe intensities and that of the sample probe intensities are compared. If the patterns are similar, the BB genotype call is accepted 404. However, if the patterns are dissimilar, the genotype call is invalidated (or filtered out).

Alternatively, similarity between the patterns of the sample probe intensities and the reference probe intensities may be also used to make genotype call directly. For example, in a preferred embodiment, the pattern of the sample probe intensities may be compared with the patterns of reference probe intensities of different genotypes, e.g. AA, AB, and BB. The genotype of the sample is determined based upon the genotype of the reference probe intensities pattern that is most similar to that of the sample probe intensities.

Reference probe intensities may be obtained in a number of different ways. For example, samples containing known genotypes may be hybridized with a genotyping array. The resulting probe intensities may be used as reference intensities. In preferred embodiments, reference intensities for a genotype are inputted from a file.

The similarity of patterns of the target probe intensities and the reference intensities may be examined in a number of ways. For example, the linear correlation, preferably a correlation coefficient, between the probe intensities and the reference intensities may be calculated. If the correlation is weak (i.e., correlation coefficient is lower that a cutoff value), the genotyping calls based upon the probe intensities may be invalidated or filtered out because it is likely that the call is due to experimental noises.

Correlation is a measure of the relation between two or more variables. Correlation coefficients can range from −1.00 to +1.00. The value of −1.00 represents a perfect negative correlation while a value of +1.00 represents a perfect positive correlation. A value of 0.00 represents a lack of correlation. The most widely-used type of correlation coefficient is Pearson r (Pearson, 1896, Regression, heredity, and Pammixia. Philosophical Transactions of the Royal Society of London, Ser. A, 187,253–318, incorporated herein by reference in its entirety), also called linear or product-moment correlation. Exemplary computer software code for calculating correlation coefficients may be found in, e.g., the Numerical Recipes (NR) books developed by Numerical Recipes Software and published by Cambridge University Press (CUP), also available online. The Numerical Recipes in C-Art of Scientific Computing-Second Edition, ISBNs 0521 43108 5, 0521 43720 2, 0521 43724 5, 0521 57608 3 and 0521 57667 5, are incorporated herein by reference in their entirety for all purposes.

Figure 5:
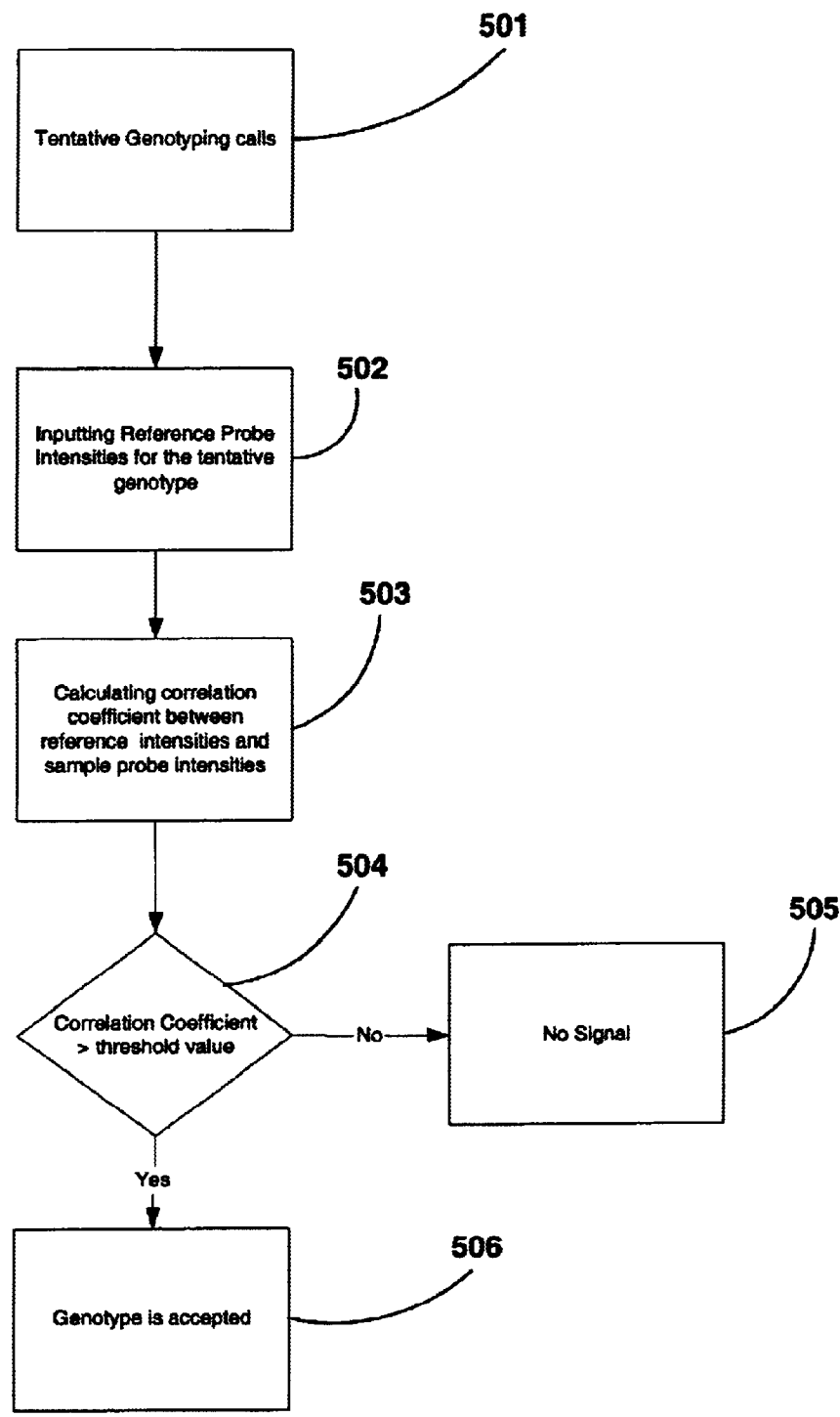
FIG. 5 illustrates a process for filtering genotype calls.

FIG. 5 shows an exemplary process for filtering out a genotyping call. A genotyping call is made based upon the relative allele signals 501. Reference intensities for the called genotype are inputted 502. A correlation coefficient between the reference intensities and probe intensities is calculated.

If the correlation coefficient is greater than a cutoff or threshold value, the genotype is accepted 506. Otherwise, the genotype identified is "filtered out" and no genotype is detected 505. The threshold value may be at least 0.6, 0.7, 0.8, 0.85, 0.9, 0.95 or 0.98. In some embodiments, the threshold value may be dependent upon the genetic marker.

The following pseudo-code illustrates computer software code for filtering genotype calls using pattern recognition:

```
CC_Mark_Genotype=CCFilter(Marker, Genotype)
    //CCFilter returns the correlation coefficient between sample probe
    //intensities and reference probe intensities.
IF (CC_Marker_Genotype=NoCC) //could not compute a correlation coefficient
    THEN Do Not Filter Genotype Call
ELSE IF (CC_Marker_Genotype<CC_Marker_Genotype_Cutoff)
    THEN Genotype Call="Filtered"
ELSE
    Do not Filter Genotype Call
```

Computer software products of the invention typically include computer readable medium having computer-executable instructions for performing the logic steps of the methods of the invention. Suitable computer readable median include floppy disk, CD-ROM/DVD/DVD-ROM, hard disk drive, flash memory, ROM/RAM, magnetic tapes and etc. The computer executable instructions may be written in any suitable computer language or combination of several languages. Suitable computer languages include C/C++ (such as Visual C/C++), Java, Basic (such as Visual Basic), Fortran, SAS and Perl.

CONCLUSION

The present invention provides methods, systems and computer software products for determining genotypes. It is to be understood that the above description is intended to be illustrative and not restrictive. Many variations of the invention will be apparent to those of skill in the art upon reviewing the above description. The scope of the invention should not be limited with reference to the above description, but should instead be determined with reference to the appended claims, along with the full scope of equivalents to which such claims are entitled.

All cited references, including patent and non-patent literature, are incorporated herein by reference in their entireties for all purposes.

What is claimed is:

1. A computer implemented method for determining the genotype of a sample comprising:
    obtaining a plurality of sample probe intensities;
    determining a tentative genotype based upon the sample probe intensities;
    calculating linear correlation coefficient between the sample probe intensities and reference probe intensities; and accepting the tentative genotype as the genotype of the sample if the linear correlation coefficient is greater than a threshold value.

2. The method of claim 1 wherein the threshold value is at least 0.8.

3. The method of claim 2 wherein the threshold value is at least 0.9.

4. The method of claim 3 wherein the threshold value is at least 0.95.

5. The method of claim 1 wherein the tentative genotype is determined based upon relative allele signal.

6. The method of claim 5 wherein the probes are immobilized on a substrate at a density of at least 400 probes per $cm^2$.

7. The method of claim 6 wherein the probes are immobilized on a substrate at a density of at least 1000 probes per $cm^2$.

8. The method of claim 7 wherein the reference genotype is a homozygous genotype.

9. The method of claim 7 wherein the reference genotype is a heterozygous genotype.

10. The method of claim 7 wherein the probes contain probes designed to be perfect match for a first genotype and a second genotype.

11. The method of claim 10 wherein the probes contain probes designed to be mismatch for a first genotype and a second genotype.

12. A computer implemented method for determining the genotype of a sample comprising:
    obtaining a plurality of sample probe intensities; and
    determining whether the pattern of the sample probe intensities is similar to that of reference probe intensities, wherein the reference probe intensities reflect hybridization between the plurality of probes and a reference sample having a reference genotype, wherein the determining comprising calculating correlation coefficient between the sample probe intensities and reference probe intensities; and indicating that the genotype of the sample is the same as the reference genotype, if the correlation coefficient is greater than a threshold value.

13. The method of claim 12 wherein the threshold value is at least 0.8.

14. The method of claim 13 wherein the threshold value is at least 0.9.

15. The method of claim 14 wherein the threshold value is at least 0.95.

16. A system for determining the genotype of a sample comprising:
    a processor; and
    a memory coupled with the least one processor, the memory storing a plurality of machine instructions that cause the processor to perform logical steps, wherein the logical steps include:
        obtaining a plurality of sample probe intensities;
        determining a tentative genotype based upon the sample probe intensities; and
        calculating linear correlation coefficient between the sample probe intensities and reference probe intensities; and accepting the tentative genotype as the genotype of the sample if the linear correlation coefficient is greater than a threshold value.

17. The system of claim 16 wherein the threshold value is at least 0.8.

18. The system of claim 17 wherein the threshold value is at least 0.9.

19. The system of claim 18 wherein the threshold value is at least 0.95.

20. The system of claim 19 wherein the tentative genotype is determined based upon relative allele signal.

21. The system of claim 20 wherein the probes are immobilized on a substrate at a density of at least 400 probes per $cm^2$.

22. The system of claim 21 wherein the probes are immobilized on a substrate at a density of at least 1000 probes per $cm^2$.

23. The system of claim 22 wherein the reference genotype is a homozygous genotype.

24. The system of claim 23 wherein the reference genotype is a heterozygous genotype.

25. The system of claim 24 wherein the probes contain probes designed to be perfect match for a first genotype and a second genotype.

26. The method of claim 25 wherein the probes contain probes designed to be mismatch for a first genotype and a second genotype.

27. A system for determining the genotype of sample comprising:

a processor; and a memory coupled with the least one processor, the memory storing a plurality of machine instructions that cause the processor to perform logical steps, wherein the logical steps include:

obtaining a plurality of sample probe intensities; and determining whether the pattern of the sample probe intensities is similar to that of reference probe intensities, wherein the reference probe intensities reflect hybridization between the plurality of probes and a reference sample having a reference genotype, wherein the determining comprising calculating correlation coefficient between the sample probe intensities and reference probe intensities; and indicating that the genotype of the sample is the same as the reference genotype, if the correlation coefficient is greater than a threshold value.

28. The system of claim 27 wherein the threshold value is at least 0.8.

29. The system of claim 28 wherein the threshold value is at least 0.9.

30. The system of claim 29 wherein the threshold value is at least 0.95.

31. A computer readable medium comprising computer-executable instructions for performing the method for determining the genotype of a sample comprising:

obtaining a plurality of sample probe intensities;

determining a tentative genotype based upon the sample probe intensities; and calculating linear correlation coefficient between the sample probe intensities and reference probe intensities; and accepting the tentative genotype as the genotype of the sample if the linear correlation coefficient is greater than a threshold value.

32. The computer readable medium of claim 31 wherein the threshold value is at least 0.8.

33. The computer readable medium of claim 32 wherein the threshold value is at least 0.9.

34. The computer readable medium of claim 33 wherein the threshold value is at least 0.95.

35. The computer readable medium of claim 34 wherein the tentative genotype is determined based upon relative allele signal.

36. The computer readable medium of claim 35 wherein the probes are immobilized on a substrate at a density of at least 400 probes per $cm^2$.

37. The computer readable medium of claim 36 wherein the probes are immobilized on a substrate at a density of at least 1000 probes per $cm^2$.

38. The computer readable medium of claim 37 wherein the reference genotype is a homozygous genotype.

39. The computer readable medium of claim 38 wherein the reference genotype is a heterozygous genotype.

40. The computer readable medium of claim 37 wherein the probes contain probes designed to be perfect match for a first genotype and a second genotype.

41. The computer readable medium of claim 40 wherein the probes contain probes designed to be mismatch for a first genotype and a second genotype.

42. A computer readable medium comprising computer-executable instructions for performing the methods comprising:

obtaining a plurality of sample probe intensities; and determining whether the pattern of the sample probe intensities is similar to that of reference probe intensities, wherein the reference probe intensities reflect the hybridization between the plurality of probes and a reference sample having a reference genotype, wherein the determining comprising calculating correlation coefficient between the sample probe intensities and reference probe intensities; and indicating that the genotype of the sample is the same as the reference genotype, if the correlation coefficient is greater than a threshold value.

43. The computer readable medium of claim 42 wherein the threshold value is at least 0.8.

44. The computer readable medium of claim 43 wherein the threshold value is at least 0.9.

45. The computer readable medium of claim 44 wherein the threshold value is at least 0.95.

* * * * *